US 6,407,109 B1

(12) United States Patent
Lubisch et al.

(10) Patent No.: US 6,407,109 B1
(45) Date of Patent: *Jun. 18, 2002

(54) PYRROLYL TETRAHYDROQUINOXALIN DIONES, THEIR PRODUCTION AND USE IN THE TREATMENT OF DISEASES

(75) Inventors: Wilfried Lubisch, Mannheim; Berthold Behl; Hans-Peter Hofmann, both of Limburgerhof; Hans-Jürgen Teschendorf, Dudenhofen, all of (DE)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/000,277
(22) PCT Filed: Aug. 26, 1996
(86) PCT No.: PCT/EP96/03759
§ 371 (c)(1),
(2), (4) Date: Jan. 27, 1998
(87) PCT Pub. No.: WO97/08168
PCT Pub. Date: Mar. 6, 1997

(30) Foreign Application Priority Data

Aug. 31, 1995 (DE) .......................................... 195 32 050

(51) Int. Cl.⁷ ..................... A61K 31/498; C07D 403/10
(52) U.S. Cl. ........................ 514/249; 514/250; 544/344; 544/354
(58) Field of Search ................................ 544/344, 354; 514/249, 250

(56) References Cited

U.S. PATENT DOCUMENTS 5,714,489 A * 2/1998 Lubisch et al. ............. 514/249
5,852,017 A * 12/1998 Lubisch et al. ............. 514/249

FOREIGN PATENT DOCUMENTS

| DE | 4340045 | * | 6/1995 |
| DE | 4428152 | * | 1/1996 |
| DE | 4436852 | * | 4/1996 |
| EP | 556393 | * | 8/1993 |
| EP | 572852 | * | 12/1993 |

OTHER PUBLICATIONS

Grant & Hackh's *Chemical Dictionary*, p. 313, 1987.*
Lees, *CNS Drugs*, 5 (1) p. 51–74 (1996).*
Lipton, *Tins*, 16, No. 12, p. 527–532 (1993).*
Doble, *Therapie*, 50, p. 319–337 (1995).*

* cited by examiner

Primary Examiner—Emily Bernhardt
(74) Attorney, Agent, or Firm—Keil & Weinkauf

(57) ABSTRACT

Pyrrolylquinoxalinediones of the formula I

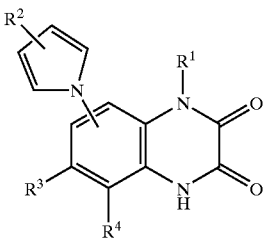

and their tautomeric and isomeric forms, and their physiologically tolerated salts, where the variables have the following meanings:

$R^1$
hydrogen, cyclohexyl
an aliphatic radical which has 1 to 4 carbon atoms and can carry the radical —COOR⁵, where $R^5$ is hydrogen or $C_1$–$C_4$-alkyl, $R^2$ —COOH, —COO—$C_1$–$C_4$, —COO—$(CH_2)_m$—Ph, —CONR⁶R⁷ and

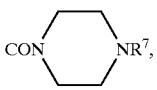

where m can be an integer from 1 to 6, $R^6$ can be hydrogen, $C_1$–$C_4$-alkyl or OH and $R^7$ can be hydrogen, $C_1$–$C_4$-alkyl,

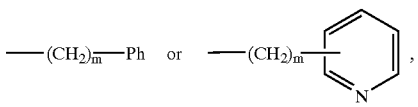

where all the phenyl or pyridyl rings present in $R^2$ can also be substituted by up to 3 of the following radicals:

$C_1$–$C_4$-alkyl, halogen, —O—$C_1$–$C_4$-alkyl, —OCF₃, —NO₂, —CN, —COOR⁵ or —CONHR⁵, $R^3$ —CF₃, —NO₂, —CN, and $R^4$
hydrogen or $R^3$ and $R^4$ can together be a fused-on benzene ring. The compounds are suitable as drugs for human and veterinary medicine.

5 Claims, No Drawings

PYRROLYL TETRAHYDROQUINOXALIN DIONES, THEIR PRODUCTION AND USE IN THE TREATMENT OF DISEASES

The present invention relates to novel pyrrolyltetrahydroquinoxalinediones, processes for the preparation thereof and the use thereof for controlling diseases.

Excitatory amino acids, in particular glutamic acid, are wide-spread in the central nervous system. The excitatory amino acid glutamate acts as transmitter substance for receptors of which various subtypes are known. One subtype is called, for example, the NMDA receptor after the specific agonist N-methyl-D-aspartate. This NMDA receptor has various binding sites for agonists and antagonists. The amino acid glycine likewise binds to the NMDA receptor and modulates the effect of the natural agonist glutamic acid. Antagonists on this glycine binding site may accordingly show antagonistic effects on the NMDA receptor and inhibit an overexcitation of this receptor.

Two other subtypes of glutamate receptors are the AMPA receptor and the kainate receptor which are each called after the specific agonists 2-amino-3-hydroxy-5-methyl-4-isoxazolepropionic acid (AMPA) and kainic acid. In a similar way to the NMDA receptor already mentioned, antagonists of these receptors can likewise inhibit overexcitation.

Elevated glutamate activity occurs in a number of neurological disorders or psychological disturbances and leads to states of overexcitation or toxic effects in the CNS.

Derivatives of quinoxaline-2,3(1H,4H)-dione II

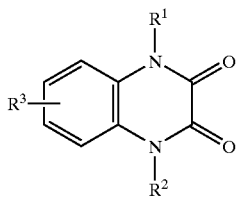

II have been described as glutamate antagonists in several publications, such as EP-A 374 534 and EP-A 260 467. Many of the known derivatives are unsubstituted in the heterocyclic quinoxaline fragment (II, $R^1$, $R^2$=hydrogen). Furthermore, derivatives where $R^1$ in II is a radical which is not hydrogen are also known. Thus, EP-A 377 112 and EP-A 374 534 have claimed N-hydroxyquinoxalines (II; $R^1$=$OR^4$). EP-A 315 959, DE-A 4 135 871, WO 91/13 878 and WO 92/07 847 describe alkyl radicals as $R^1$ in II, and the alkyl chain can also be substituted by acids, esters or amides. Alkyl acids (=$R^1$) are likewise mentioned in J. R. Epperson et al. Bioorg. & Med. Chemistry Lett. 3 (1993), 2801–4.

Quinoxalinedione derivatives II which carry a heterocycle as substituent $R^3$ are likewise known. Thus, EP-A 556 393 describes imidazoles, triazoles and pyrazoles. Quinoxaline dione derivatives which carry a pyrrolyl radical as $R^3$ have been described as glutamate antagonists in EP-A 572 852.

The substances according to the invention are suitable for treating all disorders in which a beneficial effect can be expected from glutamate antagonists.

Suitable indications are neurotoxic disturbances, especially acute and chronic oxygen/(nutrient) deficiency/states of the central nervous system. By these are meant acute hypoxic or ischemic states which occur, for example, as a consequence of cerebral infarct, subarachnoid hemorrhage or vasospasms of other etiology, also following heart/circulatory failure, eg. in cardiac arrest, cardiac arrhythmias or circulatory collapse; CNS damage following hypoglycemia, as a consequence of perinatal asphyxia or after craniocerebral trauma, spinal cord trauma, transient ischemic attacks (TIAs), prolonged reversible neurological deficits (PRINDs) and multi-infarct dementia and atherosclerotic dementia, and migraine.

Other possible indications are neurodegenerative disorders, eg. Parkinson's disease, Huntington's chorea, Alzheimer's disease, amyotropic lateral sclerosis (ALS).

Furthermore, glutamate antagonists may be suitable for use as antiepileptics, as anxiolytics and as antidepressants, and for the treatment of pain, likewise for the treatment is schizophrenia, of withdrawal symptoms in addicts, and as muscle relaxants in cases of spasticity of the skeletal muscles, eg. in multiple sclerosis (MS).

The invention relates to novel pyrrolylquinoxalinediones of the formula I

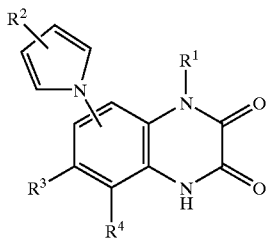

and their tautomeric and isomeric forms, and their physiologically tolerated salts, where the variables have the following meanings:

$R^1$
  hydrogen, cyclohexyl
  an aliphatic radical which has 1 to 4 carbon atoms and can carry the radical —$COOR^5$, where $R^5$ is hydrogen or $C_1$-$C_4$-alkyl, preferably —$(CH_2)_m$—$COOR^5$ with m=1–4, particularly preferably —$CH_2COOH$, $R^2$ COOH, COO—$C_1$-$C_4$, alkyl, —COO—$(CH_2)_m$—Ph, —$CONR^6R^7$ and

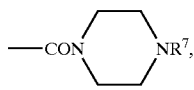

where m can be an integer from 1 to 6, $R^6$ can be hydrogen, $C_1$-$C_4$-alkyl or OH and $R^7$ can be hydrogen, $C_1$-$C_4$-alkyl,

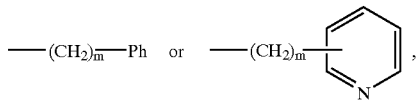

where all the phenyl or pyridyl rings present in $R^2$ can also be substituted by up to 3 of the following radicals:

$C_1$-$C_4$-alkyl, halogen, —O—$C_1$-$C_4$-alkyl, —$OCF_3$, $NO_2$, CN, —$COOR^5$ or —$CONHR^5$, $R^3$ $CF_3$, $NO_2$, CN, and $R^4$
  hydrogen and
$R^3$ and $R^4$
  can together be a fused-on benzene ring.

Preferred compounds according to the invention are quinoxaline-dione derivatives of the formula

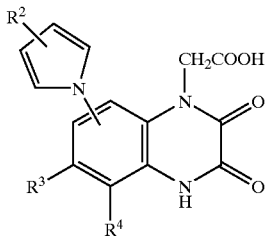

where
R$^2$
is —COOH or —CONHR$^7$ where R$^7$ is hydrogen, —CH$_2$–C$_6$H$_5$,

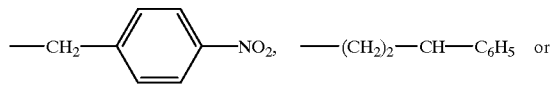

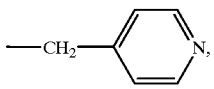

R$^3$
is NO$_2$ or CF$_3$ and R$^4$ is hydrogen, or
R$^3$ and R$^4$ are a fused-on benzene ring.
Very particularly preferred compounds are:
1-Carboxymethyl-7-(3-carboxy-1-pyrrolyl)-6-nitroquinoxaline-2,3(1H, 4H)-dione,
1-Carboxymethyl-7-(3-carboxy-1-pyrrolyl)-6-trifluoromethyl-quinoxaline-2,3-(1H, 4H)-dione,
1-Carboxymethyl-7-(3-carboxy-1-pyrrolyl)-benzo[f]quinoxaline-2,3-(1H, 4H)-dione,
7-(3-Benzylcarbamoyl-1-pytrolyl)-1-carboxymethyl-6-trifluoro-methylquinoxaline-2,3-(1H, 4H)-dione,
7-(3-Benzylcarbamoyl-1-pyrrolyl)-1-carboxymethyl-6-nitro-quinoxaline-2,3-(1H, 4H)-dione,
1-Carboxymethyl-6-nitro-7-(3-(3-phenylpropylcarbamoyl)-1-pyrrolyl)-quinoxalin-2,3(1H,4H)-dione,
1-Carboxymethyl-6-nitro-7-(3-(4-pyridinylmethylcarbamoyl)-1-pyrrolyl)quinoxaline-2,3(1H, 4H)-dione,
7-(3-Carbamoyl-1-pyrrolyl)-1-carboxymethyl-6-nitroquinoxaline-2,3(1H,4H)-dione,
1-Carboxymethyl-6-nitro-7-(3-(4-nitrobenzylcarbamoyl)-1-pyrrolyl)quinoxaline-2,3(1H, 4H)-dione.

It has been found, surprisingly, that the present pyrrole-carboxylic acid derivatives have advantages by comparison with the compounds mentioned in EP-A 572 852.

The compounds I according to the invention can be prepared in the way outlined in reaction scheme 1 below.

Synthesis of the aldehydes III has been described in EP-A 572 852. These aldehydes can be oxidized to the carboxylic acids I a according to the invention by customary literature methods which are listed, for example, in R. C. Larock, Comprehensive Organic Transformations, 1989, VCH Publisher, page 838 et seq. Particularly used for example is potassium permanganate in solvents such as acetone at 25–60° C. If there is an ester residue in R$^1$, this can subsequently be hydrolyzed with acids and bases to result in the dicarboxylic acid I d. The hydrolysis is preferably carried out with lithium hydroxide in tetrahydrofuran/water mixtures at room temperature.

Scheme 1

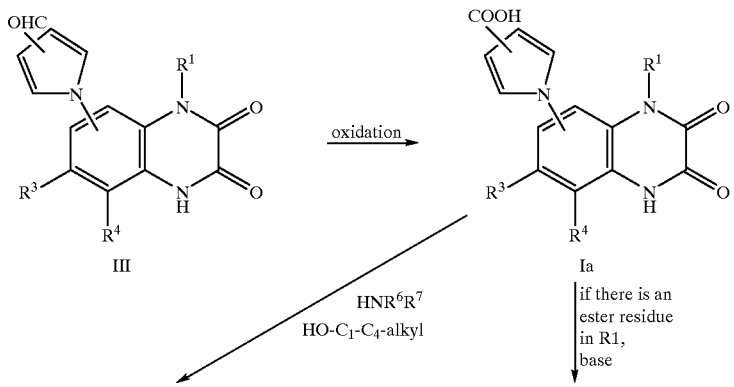

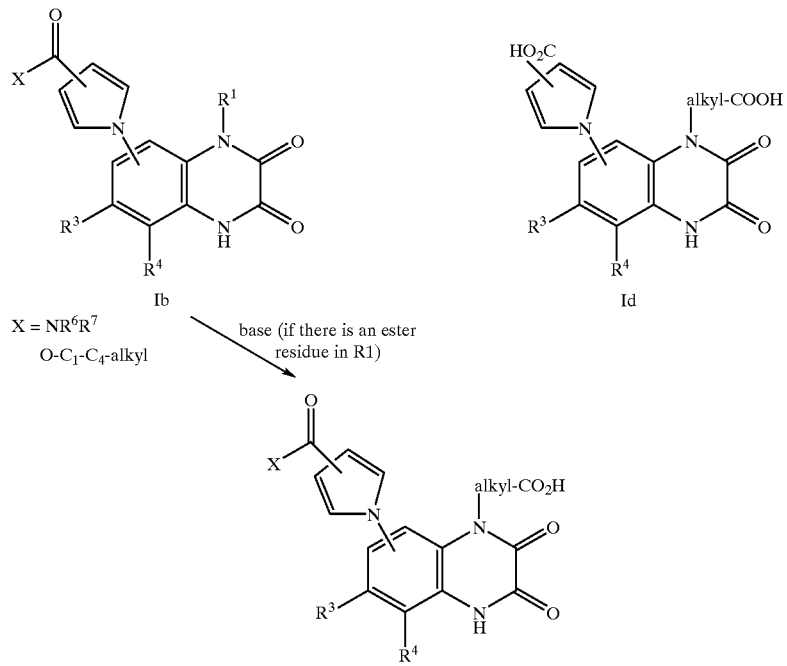

The pyrrolecarboxylic acid I a can be converted by reaction with amines or alcohols into the derivatives I b. In this case, the acid group COOH is activated in a suitable manner to COL where L is a leaving group such as azide, imidazole and others which are listed in R. C. Larock, Comprehensive Organic Transformations, New York 1989, pages 972 et seq. Subsequent addition of the reactants $HNR^6R^7$ or alcohols results in the products I b according to the invention. If the radical $R^1$ has an ester group, this can be subjected to hydrolysis similar to the above with acids and bases to give the carboxylic acid, resulting in the derivatives I c according to the invention.

The compounds according to the invention are antagonists of the excitatory amino acid glutamate, in particular antagonists of the glycine binding site of the NMDA receptor, of the AMPA receptor and of the kainate receptor.

The pharmacological activity of the compounds I was investigated on isolated membrane material from rat cerebra. For this purpose, the membrane material was treated in the presence of the compounds according to the invention with the radiolabeled substance $^3$H-2-amino-3-hydroxy-5-methyl-4-isoxazolepropionic acid ($^3$H-AMPA), [$^3$H]-glycine or [$^3$H]-kainate which bind to specific receptors (AMPA, NMDA or kainate receptors). The radioactivity of the treated membranes was then measured by scintillation counting. It was possible to determine from the bound radioactivity the amounts of bound $^3$H-AMPA, [$^3$H]-glycine or [$^3$H]-kainate, or in each case the displaced amounts of these radiolabeled substances.

The dissociation constant $K_I$ (I=inhibitor) which emerges from this and is a measure of the displacing action of the agent according to the invention was found by iterative nonlinear regression analysis using the statistical analysis system (SAS) on an IBM computer, similar to the "Ligand" program of P. J. Munson and D. Rodbard (Analytical Biochem. 107 (1980) 220, Ligand: Versatile Computerized Approach for Characterization of Ligand Binding Systems).

The following in vitro investigations were carried out:
1. Binding of $^3$H-2-amino-3-hydroxy-5-methyl-4-isoxazolepropionic Acid ($^3$H-AMPA)

To prepare the membrane material, freshly removed rat cerebra were homogenized together with 15 times the volume of a buffer solution A composed of 30 mM tris (hydroxymethyl)methylamine hydrochloride (TRIS-HCl) and 0.5 mM ethylenediaminetetraacetic acid (EDTA), pH 7.4, using an Ultra-Turrax$^R$. The suspension was centrifuged at 48000 g for 20 min. After removal of the supernatant liquid, the protein-containing membrane material in the sediment was washed three times by suspension in buffer solution A and subsequent centrifugation at 48000 g for 20 minutes each time. The membrane material was then suspended in 15 times the volume of buffer solution A and incubated at 37° C. for 30 min. The protein material was subsequently washed twice by centrifugation and suspension and stored at −70° C. until used. For the binding assay, the protein material was thawed at 37° C. and washed twice by centrifugation at 48000 g (20 min) and subsequent suspension in a buffer solution B composed of 50 mM TRIS-HCl, 0.1 M potassium thiocyanate and 2.5 mM calcium chloride, pH 7.1. Subsequently, 0.25 mg of membrane material, 0.1 $\mu$Ci of $^3$H-AMPA (60 Ci/mmol) and compound I were dissolved in 1 ml of buffer solution B and incubated on ice for 60 min. The incubated solution was filtered through a CF/B filter (from Whatman) which had previously been treated with a 0.5% strength aqueous solution of polyethyleneimine for at least 2 hours. The membrane residue was subsequently washed with 5 ml of cold buffer solution B in order to separate bound and free $^3$H-AMPA from one another. After measurement of the radioactivity of the bound $^3$H-AMPA in the membrane material by scintillation counting, the $K_I$ was determined by regression analysis of the displacement plots.

A $k_I$ of <10 $\mu$M was found for 7-(3-carboxy-1-pyrrolyl)-1-(ethoxy-carbonylmethyl)-6-nitroquinoxaline-2,3(1H,4H)-dione (Example 2). The substance is accordingly distinctly more active than the very closely related aldehyde 1-(ethoxycarbonylmethyl)-7-(3-formyl-1-pyrrolyl)-6-nitroquinoxaline-2,3(1H,4H)-dione (Example 80 in EP 572 852).

2. Binding of [³H]-glycine

To prepare the membranes for the ³H-glycine binding assay, freshly removed rat hippocampi were homogenized in 10 times the volume of preparation buffer (50 mM tris-HCl, 10 mM EDTA) using a Potter homogenizer. The homogenate was centrifuged at 48000×g for 20 min. The supernatant was discarded, and the membranes present in the pellet were washed 2× by resuspension and centrifugation at 48000×g (20 min each time). The resuspended membranes were frozen in liquid nitrogen and thawed again at 37° C. After another washing step, the membrane suspension was incubated in a shaking water bath at 37° C. for 15 min. After a further 4 washing steps (centrifugation at 48000×g for 20 minutes each time and resuspension in preparation buffer), the membranes were stored at −70° C. until used further.

The frozen membranes were thawed at 37° C. and washed 2× by centrifugation at 48000×g (20 min) and subsequent resuspension in binding buffer (50 mM tris-HCl pH 7.4, 10 mM $MgCl_2$). An incubation mixture contained 0.25 mg of protein (membranes), 25 nM ³H-glycine (16 Ci/mmol) and the substances to be tested in a total of 0.5 ml of binding buffer. The nonspecific binding was determined by adding 1 mM glycine.

After incubation at 4° C. for 60 min, bound and free ligand were separated from one another by filtration through GF/B filters and subsequent washing with about 5 ml of ice-cold binding buffer.

The radioactivity remaining on the filters is determined by liquid scintillation counting. The dissociation constants were calculated from the displacement plots using an iterative nonlinear fitting program or in accordance with the equation of Cheng and Prusoff.

3. Binding of [³H]-kainate

To prepare the membranes for the [³H]-kainate binding assay, freshly removed rat cerebra were homogenized in 15 times the volume of preparation buffer (30 mM tris-HCl pH 7.4, 0.5 mM EDTA) using an Ultra-Turrax$^R$. The homogenate was centrifuged at 48000×g for 20 min. The supernatant was discarded, and the membranes present in the pellet were washed a total of 3× by resuspension in preparation buffer and centrifugation at 48000×g (20 min each time). After the third washing step, the membranes were washed 2× by centrifugation and resuspension and stored at −70° C. until used further.

The frozen membranes were thawed at 37° C., suspended in binding buffer (50 mM tris-HCl pH 7.4) and centrifuged at 48000×g for 20 min. The membranes present in the pellet were resuspended in binding buffer. An incubation mixture contained 0.25 mg of protein (membranes), 0.058 µCi (58 Ci/mmol) of ³H-kainate and the substances to be tested in a total of 1 ml of binding buffer. The nonspecific binding was determined in the presence of 0.1 mM glutamate. After incubation on ice for 60 minutes, bound and free ligand were separated from one another by filtration through CF/B filters and subsequent washing with 5 ml of ice-cold binding buffer. The CF/B filters had previously been treated with 0.5% polyethyleneimine for at least 2 h. The displacement plots were analyzed, and the dissociation constants were calculated using a nonlinear fitting program or in accordance with the equation of Cheng and Prusoff.

To demonstrate the in vivo activity of the novel substances, results from the following test arrangements can be used:

Anticonvulsant Effect (Maximum electric shock in mice)

Tonic spasms of the rear limbs are induced in mice by a maximum electric shock. The occurrence of spasms can be antagonized by pretreatment with test substances. This antispasmodic effect is evidence of the possible use of a substance as antiepileptic.

Protection Against Cerebral Overexcitation by Excitatory Amino Acids (NMDA or AMPA antagonism in vivo, mouse)

Intracerebral administration of excitatory amino acids (=EAA) induces such massive overexcitation that this leads to spasms and to the death of the animals within a short time. These signs can be inhibited by systemic, eg. intraperitoneal, administration of centrally acting EAA antagonists. Since excessive activation of EAA receptors in the central nervous system plays a significant part in the pathogenesis of various neurological disorders, it is possible to conclude from the detected EAA antagonism in vivo that the substances can be used for the therapy of such CNS disorders. These include, inter alia, focal and global ischemias, trauma, epilepsy and various neurodegenerative disorders such as Huntington's chorea, Parkinson's disease etc.

The compounds I according to the invention are suitable as drugs for human and veterinary medicine and can be used to produce drugs for the treatment of neurodegenerative disorders and neurotoxic disturbances of the central nervous system and for producing antiepileptics, anxiolytics, antidepressants and antinociceptives.

The drug preparations according to the invention contain a therapeutically effective amount of the compounds I in addition to conventional pharmaceutical ancillary substances.

For local external use, eg. in dusting powders and ointments, the agents can be present in the usual concentrations. The agents are, as a rule, present in an amount of from 0.0001 to 1% by weight, preferably 0.001 to 0.1% by weight.

For internal use, the preparations are administered in single doses. 0.1 to 100 mg are given per kg of body weight in a single dose. The preparations can be administered in one or more doses each day, depending on the nature and severity of the disorders.

Appropriate for the required mode of administration, the drug preparations according to the invention contain conventional excipients and diluents in addition to the agent. Pharmaceutical ancillary substances possible for local external use are, for example, ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petrolatum and lanolin. Examples suitable for internal use are lactose, propylene glycol, ethanol, starch, talc and polyvinylpyrrolidone.

It is furthermore possible for antioxidants such as tocopherol and butylated hydroxyanisole and butylated hydroxytoluene, flavor-improving additives, stabilizers, emulsifiers and lubricants to be present.

The substances which are present in the preparation in addition to the agent, and the substances used in the production of the pharmaceutical preparation, are toxicologically acceptable and compatible with the agent in each case. The drug preparations are produced in a conventional way, for example by mixing the agent with the conventional excipients and diluents.

The drug preparations can be administered in various ways such as orally, parenterally, subcutaneously, intraperitoneally and topically. Thus, possible presentations are tablets, emulsions, infusion and injection solutions, pastes, ointments, gels, creams, lotions, dusting powders and sprays.

EXAMPLES

Example 1

7-(3-Carboxy-1-pyrrolyl)-1-(ethoxycarbonylmethyl)-6-trifluoro-methylquinoxaline-2,3(1H, 4H)-dione 5.0 g (12.2 mmol) of 1-(ethoxycarbonylmethyl)-7-(3-formyl-1-pyrrolyl)-6-trifluoromethylquinoxaline-2,3(1H, 4H)-dione (for synthesis, see EP 572 852, Example 70) and 3.2 g (12.2 mmol) of 18-crown-6 were refluxed in 150 ml of acetone. Then 7.7 g (48.9 mmol) of potassium permanganate were added in small portions, and the mixture was boiled for a further 30 minutes. 20 ml of water were added and the mixture was then boiled for a further 30 minutes. Subsequently, the precipitate was filtered off with suction and thoroughly washed with a mixture of tetrahydrofuran and methanol. The combined organic phases were concentrated under reduced pressure. The residue was partitioned between aqueous sodium bicarbonate solution and ethyl acetate.

The aqueous phase was then acidified with hydrochloric acid, and the resulting precipitate was filtered off with suction. 3.1 g (60%) of the product were obtained.

Melting point: >250° C.; $^1$H-NMR (D$_6$-DMSO): δ=1.2 (3H), 4.2 (2H), 5.0 (2H), 6.6 (1H), 6.9 (1H), 7.6 (1H), 7.7 (1H), 12.1 (1H) and 12.5 (1H) ppm.

The following examples according to the invention were prepared as in Example 1 from the corresponding aldehydes (synthesis in EP 572 852):

Example 2

7-(3-Carboxy-1-pyrrolyl)-1-(ethoxycarbonylmethyl)-6-nitroquin-oxaline-2,3(1H,4H)-dione Yield: 71%, melting point: >300° C.; $^1$H-NMR (D$_6$-DMSO): δ=1.2 (3H), 4.2 (2H), 5.0 (2H), 6.6 (1H), 7.0 (1H), 7.6 (1H), 7.7 (1H), 7.9 (1H), 12.2 (broad) and 12.6 (1H) ppm.

Example 3

9-(3-Carboxy-1-pyrrolyl)-1-(ethoxycarbonylmethyl)benzo[f]-quinoxaline-2,3(1H,4H)-dione Yield: 27%, melting point: 292–295° C.; $^1$H-NMR (D$_6$-DMSO): δ=1.2 (3H), 4.2 (2H), 5.1 (2H), 6.7 (1H), 7.1 (1H), 7.4–7.9 (4H), 8.8 (1H) 12.2 (1H) and 12.5 (1H) ppm.

Example 4

7-(3-carboxy-1-pyrrolyl)-1-cyclohexyl-6-nitroquinoxaline-2,3-(1H,4H)-dione

Yield: 35%, melting point: 230° C. (decomposition); $^1$H-NMR (D$_6$-DMSO): δ=1.2–2.0 (8H), 2.4 (2H), 4.5 (1H), 6.6 (1H), 7.0 (1H), 7.6 (1H), 7.8 (1H), 7.9 (1H), 12.2 (1H) and 12.5 (1H) ppm.

Example 5

7-(3-(Benzylcarbamoyl)-1-pyrrolyl)-1-cyclohexyl-6-nitroquin-oxaline-2,3(1H,4H)-dione 1.65 g (4.1 mmol) of Example 4 and 0.53 g (5 mmol) of benzylamine were dissolved in 50 ml of anhydrous dimethylformamide. At 0° C., a solution of 1.4 g of diphenylphosphoryl azide in 10 ml of anhydrous dimethylformamide was added dropwise. After about 15 minutes, 0.84 g (8.3 mmol) of triethylamine was added dropwise, and the mixture was stirred at 0° C. for about 5 h.

Subsequently the mixture was stirred at room temperature for 16 h. The reaction mixture was then concentrated under reduced pressure. The residue was partitioned between ethyl acetate and aqueous sodium bicarbonate solution, and the organic phase was separated off, dried and concentrated under reduced pressure.

Yield: 1.3 g (64%), melting point: 210° C. (decomposition); $^1$H-NMR (D$_6$-DMSO): δ=1.4–2.0 (8H), 2.4 (2H), 4.5 (2H), 6.7 (1H), 7.0 (1H), 7.1–7.4 (5H), 7.6 (1H), 7.8 (1H), 7.9 (1H), 8.5 (1H) and 12.2 (broad) ppm.

The following compounds according to the invention were prepared as in Example 5 from the corresponding carboxylic acids (Examples 1–4):

Example 6

7-(3-(4-Benzyl-1-piperazinylcarbonyl)-1-pyrrolyl)-1-ethoxy-carbonylmethyl-6-trifluoromethylquinoxaline-2,3(1H,4H)-dione Yield: 0.6 g (90%); $^1$H-NMR (D$_6$-DMSO): δ=1.2 (3H), 2.4 (4H), 3.5 (2H), 3.6 (4H), 4.2 (2H), 5.0 (2H), 6.4 (1H), 6.9 (1H), 7.2–7.4 (6H), 6.6 (1H), 6.65 (1H) and ca. 12 (broad) ppm.

Example 7

7-(3-Benzylcarbamoyl-1-pyrrolyl)-1-ethoxycarbonylmethyl-6-tri-fluoromethylquinoxaline-2,3(1H,4H)-dione Yield: 0.7 g (70%); $^1$H-NMR (D$_6$-DMSO): δ=1.2 (3H), 4.1 (2H), 4.4 (2H), 5.0 (2H), 6.7 (1H), 6.9 (1H), 7.2–7.4 (5H), 7.5 (1H), 7.65 (1H), 7.7 (1H), 8.5 (1H) and 12.5 (1H) ppm.

Example 8

7-(3-Benzylcarbamoyl-1-pyrrolyl)-1-ethoxycarbonylmethyl-6-nitro-quinoxaline-2,3(1H,4H)-dione Yield: 64%, melting point: 223° C. (decomposition); $^1$H-NMR (D$_6$-DMSO): δ=1.2 (3H), 4.1 (2H), 4.2 (2H), 5.1 (2H), 6.5 (1H), 6.7 (1H), 6.9 (1H), 7.1–7.7 (6H), 7.8 (1H), 8.0 (1H) and 8.5 (1H) ppm.

Example 9

1-Ethoxycarbonylmethyl-6-nitro-7-(3-(4-(2-phenylethyl)-1-piperazinylcarbonyl-1-pyrrolyl)quinoxaline-2,3(1H,4H)-dione Yield: 58%, melting point: >160° C. (decomposition); $^1$H-NMR (D$_6$-DMSO): δ=1.2 (3H), 2.6 (2H), 2.8 (2H), 3.2–3.6 (8H), 4.2 (2H), 5.1 (2H), 6.4 (1H), 6.9 (1H), 7.1–7.4 (6H), 7.6 (1H) and 7.9 (1H) ppm.

Example 10

1-Ethoxycarbonylmethyl-6-nitro-7-(3-(3-phenylpropylcarbamoyl)-1-pyrrolyl)quinoxaline-2,3-(1H,4H)dione Yield: 69%, melting point: 224° C. (decomposition); $^1$H-NMR (D$_6$-DMSO): δ=1.2 (3H), 1.8 (2H), 2.6 (2H), 3.2 (2H), 4.1 (2H), 5.0 (2H), 6.7 (1H), 6.9 (1H), 7.1–7.4 (5H), 7.5 (1H), 7.6 (1H), 7.9 (1H), 7.95 (1H) and 11.8 (broad) ppm.

Example 11

1-Ethoxycarbonylmethyl-6-nitro-7-(3-(4-pyridinylmethylcarbamoyl)-1-pyrrolyl)quinoxaline-2,3(1H,4H)-dione Yield: 71%, melting point: >300° C.; $^1$H-NMR (D$_6$-DMSO): δ=1.2 (3H), 4.2 (2H), 4.4 (2H), 5.0 (2H), 6.7 (1H), 6.9 (1H), 7.2–7.5 (4H), 7.6 (1H), 8.5 (2H) and 8.6 (1H) ppm.

Example 12

1-Ethoxycarbonylmethyl-6-nitro-7-(3-(4-nitrobenzylcarbamoyl)-1-pyrrolyl)quinoxaline-2,3(1H,4H)-dione Yield: 31%, melting point: >300° C.; $^1$H-NMR ($D_6$-DMSO): δ=1.2 (3H), 4.2 (2H), 4.6 (2H), 5.1 (2H), 6.7 (1H), 7.0 (1H), 7.4–7.6 (3H), 7.7 (1H), 7.9 (1H), 8.2 (2H), 8.7 (1H) and 12.5 (broad) ppm.

Example 13

7-(3-Carbamoyl-1-pyrrolyl)-1-ethoxycarbonylmethyl-6-nitroquinox-aline-2,3(1H,4H)-dione Yield: 80%, melting point: >300° C.; $^1$H-NMR ($D_6$-DMSO): δ=1.2 (3H), 4.2 (2H), 5.1 (2H), 6.6 (1H), 6.9 (1H), 6.95 (1H), 7.4 (1H), 7.5 (1H), 7.7 (1H), 7.9 (1H) and 12.5 (1H) ppm.

Example 14

1-Carboxymethyl-7-(3-carboxy-1-pyrrolyl)-6-nitroquinoxaline-2,3(1H,4H)-dione 1.5 g (3.8 mmol) of Example 2 were dissolved in 50 ml of tetrahydrofuran, and a solution of 0.27 g (11.3 mmol) of lithium hydroxide in 25 ml of water was added. The mixture was stirred at room temperature for 1 h. Then the organic solvent was removed under reduced pressure, and the resulting aqueous phase was made slightly acidic with hydrochloric acid. The resulting precipitate was filtered off with suction and recrystallized from a little isopropanol.

Yield: 0.5 g (86%), melting point: >300° C. (decomposition); $^1$H-NMR ($D_6$-DMSO): δ=5.0 (2H), 6.6 (1H), 7.0 (1H), 7.6 (1H), 7.7 (1H), 8.0 (1H) and 12.5 (broad) ppm.

The following compounds according to the invention were prepared as in Example 14 from the appropriate carboxylic esters.

Example 15

1-Carboxymethyl-7-(3-carboxy-1-pyrrolyl)benzo[f]quinoxaline-2,3(1H, 4H)-dione

Yield: 72%, melting point: >300° C.; $^1$H-NMR ($D_6$-DMSO): δ=5.1 (2H), 6.7 (1H), 7.1 (1H), 7.3–7.9 (5H), 8.7 (1H) and 12.5 (broad) ppm.

Example 16

1-Carboxymethyl-7-(3-carboxy-1-pyrrolyl)-6-trifluoromethylquinox-aline-2,3-(1H,4H)-dione Yield: 36%, melting point: >170° C. (decomposition); $^1$H-NMR ($D_6$-DMSO): δ=4.9 (2H), 6.6 (1H), 6.9 (1H), 7.5 (1H), 7.65 81H), 7.7 (1H), ca. 12.3 (broad) and 12.5 (1H) ppm.

Example 17

7-(3-(4-Benzyl-1-piperazinylcarbonyl)-1-pyrrolyl)-1-carboxy-methyl-6-trifluoromethylquinoxaline-2,3(1H,4H)-dione Yield: 90%, melting point: >230° C. (decomposition); $^1$H-NMR ($D_6$-DMSO): δ=2.4 (4H), 3.4–3.7 (6H), 4.9 (2H), 6.4 (1H), 6.9 (1H), 7.2 (1H), 7.2–7.4 (5H), 7.6 (1H), 7.65 (1H) and 12.5 (broad) ppm.

Example 18

7-(3-Benzylcarbamoyl-1-pyrrolyl)-1-carboxymethyl-6-trifluoro-methylquinoxaline-2,3(1H,4H)-dione Yield: 70%, melting point: >200° C. (decomposition); $^1$H-NMR ($D_6$-DMSO): δ=4.6 (2H), 5.1 (2H), 6.75 (1H), 6.9 (1H), 7.2–7.4 (5H), 7.5 (1H), 7.7 (1H) and 7.8 (1H) ppm.

Example 19

7-(3-Benzylcarbamoyl-1-pyrrolyl)-1-carboxymethyl-6-nitroquinox-aline-2,3(1H,4H)-dione Yield: 52%, melting point: >200° C. (decomposition); $^1$H-NMR ($D_6$-DMSO): δ=4.4 (2H), 5.0 (2H), 6.7 (1H), 7.0 (1H), 7.2–7.4 (5H), 7.5 (1H), 7.7 (1H), 7.9 (1H), 8.5 (1H) and ca. 12.5 (broad) ppm.

Example 20

1-Carboxymethyl-6-nitro-7-(3-(4-(2-phenylethyl)-1-piperazinyl-carbonyl)-1-pyrrolyl)quinoxaline-2,3(1H, 4H)-dione Yield: 76%, melting point: >250° C. (decomposition); $^1$H-NMR ($D_6$-DMSO): δ=2.6 (4H), 2.7 (2H), 2.8 (2H), 3.7 (4H), 4.9 (2H), 6.4 (1H), 6.9 (1H), 7.1–7.4 (6H), 7.6 (1H), 8.0 (1H) and 25 12.5 (broad) ppm.

Example 21

1-Carboxymethyl-6-nitro-7-(3-(3-phenylpropylcarbamoyl)-1-pyrrolyl)quinoxaline-2,3(1H,4H)-dione Yield: 80%, melting point: 224–227° C. (decomposition); $^1$H-NMR ($D_6$-DMSO): δ=1.8 (2H), 2.6 (2H), 3.2 (2H), 5.0 (2H), 6.7 (1H), 6.9 (1H), 7.1–7.4 (5H), 7.5 (1H), 7.7 (1H), 7.9 (1H), 8.0 (1H) and 12.5 (broad) ppm.

Example 22

1-Carboxymethyl-6-nitro-7-(3-(4-pyridinylmethylcarbamoyl)-1-pyrrolyl)quinoxaline-2,3(1H,4H)-dione Yield; 64%, melting point: >300° C.; $^1$H-NMR ($D_6$-DMSO): δ=4.5 (2H), 5.0 (2H), 6.7 (1H), 7.0 (1H), 7.4 (2H), 7.5 (1H), 7.6 (1H), 7.9 (1H), 8.6 (2H), 8.7 (1H) and 12.5 (broad) ppm.

Example 23

7-(3-Carbamoyl-1-pyrrolyl)-1-carboxymethyl-6-nitroquinox-aline-2,3-(1H,4H)-dione Yield: 50%, melting point: >300° C.; $^1$H-NMR ($D_6$-DMSO): δ=5.0 (2H), 6.7 (1H), 6.9 (1), 6.95 (1H), 7.5 (1H), 7.7 (1H), 7.9 (1H) and 12.6 (broad) ppm.

Example 24

1-Carboxymethyl-6-nitro-7-(3-(4-nitrobenzylcarbamoyl)-1-pyrrolyl)quinoxaline-2,3(1H,4H)-dione Yield: 89%, melting point: >210° C. (decomposition); $^1$H-NMR ($D_6$-DMSO): δ=3.7 and 3.9 (2H), 4.7 and 4.8 (2H), 7.1 (1H), 7.5 (2H), 7.8–8.2 (6H) and 5.5 (1H) ppm.

We claim:

1. A quinoxalinedione derrivative of the formula:

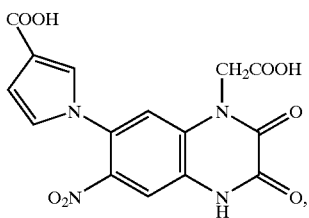

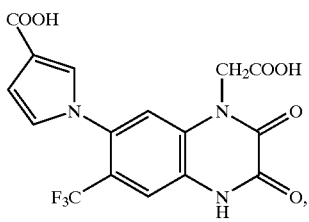

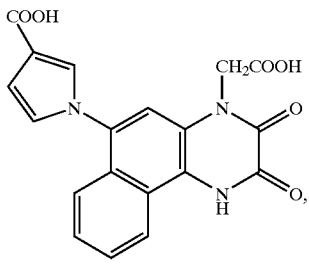

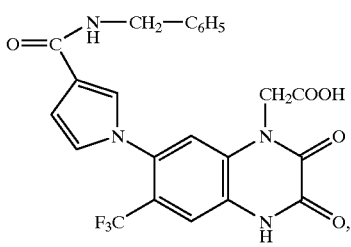

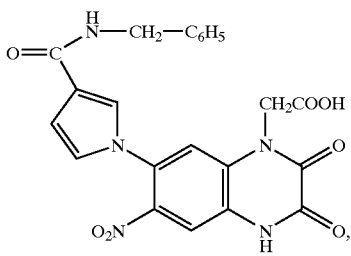

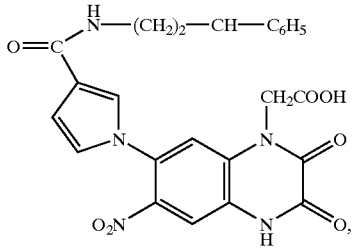

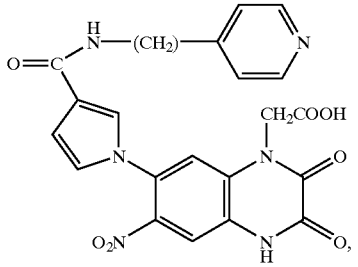

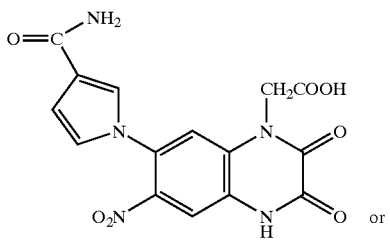 or

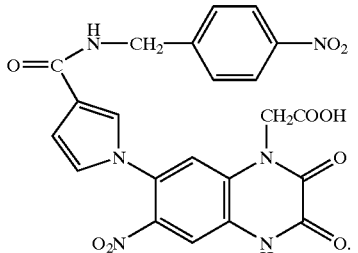

2. A method of treating Parkinson's disease, in a mammal, which method comprises administering an effective amount of the quinoxalinedione derivative, as defined in claim 1 to said mammal.

3. A method of treating epilepsy, anxiety, or depression, in a mammal, which method comprises administering an effective amount of the quinoxalinedione derivative, as defined in claim 1 to said mammal.

4. A method of treating ischemia or hypoxia in a mammal, which method comprises administering an effective amount of the quinoxalinedione derivative, as defined in claim 1 to said mammal.

5. A pharmaceutical composition comprising an effective amount of the quinoxalinedione derivative, as defined in claim 1 and a pharmaceutically acceptable carrier.

* * * * *